United States Patent [19]

Freudewald et al.

[11] Patent Number: 4,755,503

[45] Date of Patent: Jul. 5, 1988

[54] FRAGRANCE COMPOSITIONS CONTAINING 2,4,6-TRIBROMO-3-METHYLANISOLE METHYLANISOLE

[75] Inventors: Joachim E. Freudewald, Basking Ridge; Kenneth L. Purzycki, Lake Parsippany; Joseph A. Virgilio, Wayne, all of N.J.

[73] Assignee: Givaudan Corporation, Clifton, N.J.

[21] Appl. No.: 111,897

[22] Filed: Oct. 21, 1987

[51] Int. Cl.[4] .................. A61K 7/46

[52] U.S. Cl. .................. 512/20; 512/8; 512/25; 568/610

[58] Field of Search .................. 512/20, 25, 8; 568/610, 568/608

[56] References Cited

PUBLICATIONS

K. Adachi, Bull. Chem. Soc. Japan, 46, 688 (1973).

Chemical Abstracts 22, 3643[5] (1928) for E. Bures et al. Casopis Ceskoslovenskeho Lekarnictva 6, 117,129 (1926).

*Primary Examiner*—Werren B. Lone

*Attorney, Agent, or Firm*—Robert F. Tavares; Linda A. Vag

[57] ABSTRACT

Fragrance compositions prepared by adding thereto an olfactorily effective amount of substantially pure 2,4,6-tribromo-3-methylanisole are disclosed.

2 Claims, No Drawings

FRAGRANCE COMPOSITIONS CONTAINING 2,4,6-TRIBROMO-3-METHYLANISOLE METHYLANISOLE

BACKGROUND OF THE INVENTION

1. Field of the Invention

Odorant Compositions

2. Background Art

The art of creating a fragrance involves blending varying amounts of a number of substances each having individual odor characteristics, to produce a composition which has the desired olfactive effect. The amount of any particular substance present in a fragrance will of course be dependent upon the effect the perfumer wishes to achieve by the use of that substance. For example, a substance may be used in higher concentrations when a perfumer wishes to have the odor character of that substance provide or support a dominant odor in the fragrance. When more subtle effects are to be achieved, a perfumer will often prefer to use a substance in lesser quantities so that its odor will not disturb the dominant odor notes provided by the other fragrance materials, but will provide subtle effects on those dominant odor notes. For example, when a perfumer desires to make a fragrance appear to be more uniformly blended, fuller, rounder, and/or more natural, i.e., to "finish" the fragrance, he or she will often prefer to use a substance that can achieve these subtle effects with a minimal amount of that substance present. Perfumers are always seeking new odorant compounds which can be used in small quantities to provide these desirable finishing effects, particularly odorants which can provide these subtle effects in the creation of natural florals.

The 2,4,6-tribromo-3-methylanisole used in this invention is a known compound which has been reported in the prior art. [See for example, K. Adachi, Bull. Chem. Soc. Japan, 46, 688, 1973; E. Bures et al., Casopis Ceskoslovenskeho Lekarnictva 6, 117 and 129 (1926) (Chem. Abs. 22, $3643^5$, 1928).] No uses have been disclosed for the compound.

SUMMARY OF THE INVENTION

This invention teaches fragrance compositions and methods for preparing fragrance compositions utilizing 2,4,6-tribromo-3-methylanisole, I.

Compound I has an odor which can be described as very tenacious, long lasting and intense. The odor characteristics perceived have been found to be dependent upon the concentration at which compound I is being evaluated. For example, undiluted, I is perceived as having a musty, damp, earthy-green odor, while upon dilution, it develops a floral characteristic which is described as being most closely associated with the character of a rose. These odor properties of compound I can be used to good advantage in a wide variety of fragrance compositions to provide odor notes, to support, enhance or blend dominant odor notes of other fragrance materials, and/or to add a "finishing" naturalness and strength to the fragrance. The compound I is particularly valuable for use in floral compositions where small quantities can be used to add a natural "finishing" quality to the fragrance.

DESCRIPTION OF THE PREFERRED EMBODIMENTS

Compound I may be synthesized by known methods. For example a chemist may brominate meta-cresol followed by methylation of the resultant phenol or may brominate the cresyl methyl ether, 3-methylanisole, as described in Example I herein.

The odor properties of 2,4,6-tribromo-3-methylanisole make it a very versatile compound which can be used in a wide variety of compositions. At higher concentrations, compound I can be used to provide a dominant note to a composition or to support or enhance a dominant note (e.g. spicy, woody or leathery notes) which are due to other fragrance materials. When used at lower concentrations, compound I is found to provide a "finishing" quality which is described as adding a naturalness or fullness to the composition. This latter effect is particularly beneficial in floral compositions. The earthy-green notes of compound I add a note of naturalness found in the natural floral, giving the effect of presenting the whole flower in a natural setting, i.e., with leaf and stem present. This effect, which is most closely associated with the natural rose, is hard to achieve in a synthetic rose base and usually requires the use of more than one compound. Concentrations of about 0.05% to 1.0% of compound I, have been found to add this natural quality to rose-type compositions, i.e., one can take an ordinary rose, add a "touch" of I and make it more complete, more natural, more full and better finished. (See Example IIA)

Other florals such as muguet, honeysuckle, lilac and the like also attain a better, natural floralcy with the addition of 2,4,6-tribromo-3-methylanisole. In a muguet base (Example IIB) the elements of ylang-ylang and rose aromatics were made more harmonious (blended) by the presence of 0.07% of compound I. The introduction of a green-earthy note made the floral fragrance of the muguet appear more natural. Non-florals such as pine, citrus, wood and green (e.g., herbal) compositions likewise can be made more natural and stronger by the addition of small quantities of compound I.

As the concentration of compound I in a fragrance composition is increased, the odor character of compound I can provide interesting effects on the dominant odors of the composition. Compound I can be used for the effects of its earthy character on spice notes and wood notes which themselves may have a degree of this quality. When used at a concentration of 3.5%, compound I was found to have an interesting effect on a carnation base (Example IIC) wherein the orris-woody notes of methyl-ionone and the spicy notes of eugenol predominated. Compound I had the desirable effect of enhancing and blending the orris-spicy quality of the carnation base. A basically inexpensive wood base (Example IID) in which Vetiver (woody) and orris notes predominated was dramatically improved by the presence of 6.5% of I. Both the dominant elements of Vetiver and orris were greatly enhanced, making the base seem richer and achieving a quality that is usually achieved by the use of more expensive components. The base was much more intense, stronger, more diffusive and was described as having more "presence".

The perfume arts are, of course, subjective and the amounts used as well as the scope of such use, will depend ultimately upon the imagination and personal preferences of the perfumer. Amounts used will also depend on the type of fragrance and the strength of other ingredients present. It is well within the skill of the perfumer to add the compound in varying amounts to determine the preferred range.

For the most part, 2,4,6-tribromo-3-methylanisole can be used in fragrance formulations in a practical range of from 0.01% to 20%. A lower range of 0.05% to 1.0% is preferred when it is desired to provide a "finishing" effect to the composition. Higher concentrations of up to 20% are preferred when it is also desired to provide a dominant note or to support a dominant note in the composition. This will vary of course depending upon the type of fragrance formula involved. Concentrations above 20%, even as high as 80 or 90% may be used for special effects.

The compound can be used to prepare fragrance bases for the preparation of perfumes and toilet waters by adding the usual alcoholic and aqueous diluents thereto. Approximately 15-20% by weight of base would be used for perfumes and approximately 3-5% for toilet waters.

Similarly, the base compositions can be used to odorize soaps, detergents, cosmetics, or the like. In these instances, a base concentration of from about 0.5 to 2% by weight can be used.

ILLUSTRATION OF THE PREFERRED EMBODIMENTS

The following examples are provided for the sole purpose of illustrating the preferred embodiments of this invention and they should not be construed as limiting. Unless otherwise indicated, perfume ingredients are given in parts per thousand by weight. Where the material used is better known by its common name, trademark or tradename, such a name is used with the chemical name being given in parenthesis.

EXAMPLE I

Preparation of 2,4,6-Tribromo-3-methylanisole, I

Bromine, 300 g, was slowly added at ambient temperature, to a mixture of 61 g (0.5 m) of 3-methylanisole and 5 g of a mixture of silver sulfate in 300 mL of 93% sulfuric acid. (Any equivalent silver salt, e.g., carbonate, acetate, etc. may be used.) The reaction mixture was stirred overnight (16 hours) at room temperature after which time the excess bromine was removed by a stream of air passed through the resultant suspension. The suspension was then added to 500 g of ice, the solid material was filtered off, air dried, and then added to 300 mL of hot isopropanol. The silver sulfate, formed in the reaction, was removed by filtration after which 95 g of product was recovered by crystallization from the hot alcohol.

Analysis: (GLC, 10% SE-30 silicon column $\frac{1}{4}$ inch × 6 ft. 180° C.) 98.7% 2,4,6-tribromo-3-methylanisole; m.p.: 71.5°-73.5° C.; yield: 52.3 mole percent.

EXAMPLE II

Use of 2,4,6-Tribromo-3-methylanisole, I, in Fragrance Compositions

A. Rose Base

| Component | Parts/thousand |
|---|---|
| Phenyl Ethyl Alcohol | 265 |
| Geraniol Pure | 335 |
| Citronellol Extra | 320 |
| Rosacetol TM (Givaudan) (α-[Trichloromethyl] benzyl acetate) | 65 |
| Viridine TM (Givaudan) (Phenyl acetaldehyde dimethylacetal) | 7 |
| Dipropylene Glycol | 3 |
| 2,4,6-Tribromo-3-methylanisole, I, (10% Benzyl Benzoate) | 5 |
| | 1,000 |

Five parts of a 10% solution of compound I in benzyl benzoate (0.05%) were used in the above rose composition. The earthy-green character of I was found to add an attractive natural fullness to the rose character of what is an inexpensive rose base. Because of the strength of I, the strength of the base was also improved.

B. Muguet Base

| Component | Parts/thousand |
|---|---|
| Phenyl Ethyl Alcohol | 100 |
| Geraniol Pure | 100 |
| Citronellol Extra | 200 |
| Benzyl Acetate Extra | 50 |
| Methyl Dihydrojasmonate | 200 |
| Ylang-Ylang Bourbon | 20 |
| Lilial ® (Givaudan) (p-t-Butyl-α-methylhydrocinnamaldehyde) | 200 |
| Linalool | 100 |
| Sandalore ® (Givaudan) [5-(2,2,3-trimethylcylopent-3-en-l-yl)-3-methylpentan-2-ol] | 10 |
| Dipropylene Glycol | 13 |
| 2,4,6-Tribromo-3-methylanisole, I, (10% Benzyl Benzoate) | 7 |
| | 1000 |

Seven parts of a 10% solution of compound I in benzyl benzoate (0.07%) were used in the above muguet composition. The elements of ylang-ylang and the rose aromatics were made more harmonious (better blended) by the presence of I. A green-earthy note was introduced which had the effect of making the floral fragrance of the muguet appear more natural. The muguet without commpound I was perceived as being thinner, simpler, and the elements of ylang-ylang and the rose aromatics were perceived as not being fully integrated into the muguet complex.

C. Carnation Base

| Component | Parts/thousand |
|---|---|
| Phenyl Ethyl Alcohol | 50 |
| Geraniol Pure | 100 |
| Amyl Cinnamic Aldehyde | 150 |
| Benzyl Acetate Extra | 100 |
| Linalool | 50 |
| Eugenol | 200 |
| Ethyl Vanillin | 3 |
| Benzyl Salicylate | 100 |
| Isoraldeine ® 70 (Givaudan) (Methyl Ionone) | 50 |
| Indole Pure | 2 |
| p-t-Butylcyclohexylacetate | 50 |
| Dipropylene Glycol | 110 |
| 2,4,6-Tribromo-3-methylanisole, I | 35 |
| | 1000 |

Thirty-five parts of compound I (3.5%) were used in the above carnation composition. Compound I had the very desirable effect of enhancing both the orris-woody notes of methyl ionone and the spicy notes of the eugenol. Without I the orris and spice notes appeared to be much weaker in strength and the fragrance appeared to be less natural.

D. Wood Base

| Component | Parts/thousand |
|---|---|
| Vetiver Haiti oil | 100 |
| Vetynal ® (Givaudan) (Acetylcaryophyllene | 400 |
| Isoraldeine ® 70 (Givaudan) (Methyl Ionone) | 200 |
| Methyl Cedryl Ketone | 100 |
| Dipropylene Glycol | 135 |
| 2,4,6-Tribromo-3-methylanisole, I | 65 |
| | 1000 |

Sixty-five parts of compound I (6.5%) were used in the above wood composition. The composition without I is an inexpensive base built around Vetiver (woody) and orris notes which are perceived as unblended. The presence of compound I blended and enhanced the effect of both these notes making the base seem richer and achieving a quality that is usually achieved by the use of more expensive components. The intensity of the base as a whole was dramatically improved. The base was described as being stronger, more diffusive and having more "presence" than the base without compound I.

We claim:

1. A fragrance composition comprising an olfactorily effective amount of substantially pure 2,4,6-tribromo-3-methylanisole and at least one other olfactive substance.

2. A method for improving the odor of a fragrance composition which comprises adding thereto an olfactorily effective amount of substantially pure 2,4,6-tribromo-3-methylanisole.

* * * * *

UNITED STATES PATENT AND TRADEMARK OFFICE
CERTIFICATE OF CORRECTION

PATENT NO. : 4,755,503

DATED : July 5, 1988

INVENTOR(S) : Joachim E. Freudewald et al.

It is certified that error appears in the above-identified patent and that said Letters Patent is hereby corrected as shown below:

On the Title page, section [54] and at column 1, lines 1-3, correct the Title "FRAGRANCE COMPOSITIONS CONTAINING 2,4,6-TRIBROMO-3-METHYLANISOLE METHYLANISOLE" to read -- FRAGRANCE COMPOSITIONS CONTAINING 2,4,6-TRIBROMO-3-METHYLANISOLE --.

Signed and Sealed this

Tenth Day of July, 1990

*Attest:*

HARRY F. MANBECK, JR.

*Attesting Officer*

*Commissioner of Patents and Trademarks*